US006951873B1

(12) United States Patent
Lundy

(10) Patent No.: US 6,951,873 B1
(45) Date of Patent: Oct. 4, 2005

(54) METHODS FOR TREATING AGE-RELATED BEHAVIORAL DISORDERS IN COMPANION ANIMALS

(75) Inventor: Kristin M. Lundy, Groton, CT (US)

(73) Assignee: Pfizer Inc., New York, NY (US)

( * ) Notice: Subject to any disclaimer, the term of this patent is extended or adjusted under 35 U.S.C. 154(b) by 0 days.

(21) Appl. No.: 09/518,408

(22) Filed: Mar. 3, 2000

Related U.S. Application Data

(60) Provisional application No. 60/131,243, filed on Apr. 27, 1999.

(51) Int. Cl.[7] .................... A61K 31/445; A61K 31/424; A61K 31/42

(52) U.S. Cl. ........................ 514/322; 514/324; 514/372; 514/373; 514/374; 514/375; 514/376; 514/377

(58) Field of Search ................................ 514/322, 324, 514/372–377

(56) References Cited

U.S. PATENT DOCUMENTS

| | | | |
|---|---|---|---|
| 3,536,809 A | 10/1970 | Applezweig | 424/28 |
| 3,598,123 A | 8/1971 | Zaffaroni | 128/268 |
| 3,630,200 A | 12/1971 | Higuchi | 128/268 |
| 3,847,770 A | 11/1974 | Radlowe et al. | 204/159.23 |
| 3,916,899 A | 11/1975 | Theeuwes et al. | 128/260 |
| 4,008,719 A | 2/1977 | Theeuwes et al. | 128/260 |
| 4,687,610 A | 8/1987 | Vassilatos | 264/211.14 |
| 4,769,027 A | 9/1988 | Baker et al. | 424/493 |
| 5,059,595 A | 10/1991 | Le Grazie | 424/462 |
| 5,073,543 A | 12/1991 | Marshall et al. | 514/21 |
| 5,120,548 A | 6/1992 | McClelland et al. | 424/473 |
| 5,354,566 A | 10/1994 | Addesso et al. | 426/19 |
| 5,494,908 A * | 2/1996 | O'Malley et al. | 514/228.2 |
| 5,538,984 A * | 7/1996 | Villalobos et al. | 514/322 |
| 5,591,767 A | 1/1997 | Mohr et al. | 514/413 |
| 5,639,476 A | 6/1997 | Oshlack et al. | 424/460 |
| 5,674,533 A | 10/1997 | Santus et al. | 424/493 |
| 5,733,566 A | 3/1998 | Lewis | 424/426 |
| 5,750,542 A | 5/1998 | Villalobos et al. | 514/322 |

FOREIGN PATENT DOCUMENTS

WO 9217475 10/1992

OTHER PUBLICATIONS

Giovannini et al., "Effect of subchronic treatment with metrifonate and tacrine on brain cholinergic function in aged F344 rats", abstract to Eur. J. Pharmacol. 354(1), pp. 17–24, 1998.*
Bryson, et al., "Donepezil", Abstract from Drugs Aging 10(3), pp. 234–239, 1997.*
Cheng, et al., "Huperzine a, a novel promising acetylcholinesterase inhibitor", abstract to NeuroReport, 8(1), pp. 97–101, 1996.*
Leonard, et al., "Pontine nitric oxide modulates acetylcholine release, rapid eye movement sleep generation, and respiratroy rate", Journal of Neuroscience, vol. 17, No. 2, pp. 774–785, 1997.*
Cummings, et al.; β–Amyloid Accumulation Correlates with Cognitive Dysfunction in the Aged Canine; Neurobiology of learning and Memory; vol. 66, pp 11–23, (1996).
Ruehl, et al.; Canine Cognitive Dysfunction; Psychopharmacology of Animal Behavior Disorders; pp 283–304, (1998).
Corey–Bloom, et al.; Monoamine Oxidase Inhibitors in Alzheimer's Disease; Monoamine Oxidase Inhibitors in Neurological Diseases; pp. 279–294 (1994).
Finnegan; Inhibition of Monoamine Oxidase B and the Neuroprotective Effects of Selegiline; Monamine Oxidase Inhibitors in Neurological Diseases; pp. 210–216 (1994).
Hart, et al.; Selecting, Raising, and Caring for Dogs to avoid Problem Aggression; JAVMA, vol. 210, No. 8; pp 1129–1134 (1997).
Ruehl, et al.; Canine Cognitive Dysfunction as a Model for Human age–related Cognitive Decline, Dementia and Alzheimer's Disease; Progress in Brain Research; vol. 106: 217–225, (1995).
Ruehl, et al.; Therapeutic Actions of L–Deprenyl in Dogs: A Model of Human Brain Aging; Advances in Pharmacology; vol. 42: pp 316–319, (1998).
E. Head, et al.; Spatial Learning and Memory as a Function of Age in the Dog; Behavioral Neuroscience; vol. 109, pp 851–858 (1995).
E. Head, et al.; The Effects of L–Deprenyl on Spatial Short Term Memory in Young and aged Dogs; Prog. Neuro–Psychopharmacol. & Biol. Psychiatry; vol. 20, pp 515–530, (1996).
Mimori, et al.; Abnormalities of Acetylcholinesterase in Alzheimer's Disease with Special Reference to effect of Acetylcholinesterase Inhibitor; Behav. Brain Res. vol., 83, pp. 25–30, (1997).
Ellman, et al.; A New and Rapid Colorimetric Determination of Acetylcholinesterase Activity; Biochemical Pharmacology; vol. 7, pp 88–95 (1960).

* cited by examiner

Primary Examiner—Dwayne Jones
(74) Attorney, Agent, or Firm—Peter C. Richardson; Jeffrey N. Myers; Lorraine B. Ling

(57) ABSTRACT

Methods for the treatment of age-related behavioral disorders in companion animals are disclosed. These comprise administering to a companion animal in need of such treatment a therapeutically effective amount of an acetylcholinesterase inhibitor. A preferred acetylcholinesterase inhibitor is a compound of Formula 1:

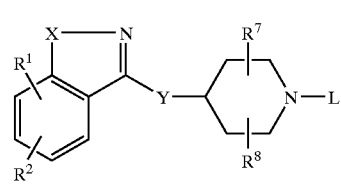

Formula 1

Pharmaceutical compositions and dosage forms comprising a compound of Formula 1 are also disclosed.

16 Claims, No Drawings

METHODS FOR TREATING AGE-RELATED BEHAVIORAL DISORDERS IN COMPANION ANIMALS

This application claims the benefit of priority of U.S. Provisional Application Ser. No. 60/131,243, filed Apr. 27, 1999.

FIELD OF INVENTION

This invention relates to methods and compositions useful in the treatment of age-related behavioral disorders in cats and dogs.

BACKGROUND OF THE INVENTION

Cognitive dysfunction syndrome (CDS) is an age-related behavioral disorder which is observed in cats and dogs and is characterized by a decline in cognitive ability that cannot be attributed to an unrelated general medical condition such as neoplasia, infection, or organ failure. In dogs, symptoms of age-related behavioral disorders such as CDS include memory loss, which may be manifested by disorientation and/or confusion, altered interaction with family members, changes in sleep-wake cycle, decreased activity level and frequent inappropriate elimination. Similar symptoms can be observed in cats suffering from CDS.

The cause of CDS is unknown. Studies have shown that its symptoms increase with age, and many pathological changes occur in aging dogs and cats that can theoretically lead to CDS. One such change, which has been correlated with CDS in dogs, is the formation of β-amyloid plaques. See, e.g., Cummings, B. J., et al., *Neurobiol. Learning & Memory* 66:11–23 (1996). Another change is the decline in activity of several neurotransmitters, including acetylcholine, serotonin, norepinephrine, and dopamine. See, e.g., Ruehl, W. W., et al., *Psychopharmacology of Animal Behavior Disorders*, Dodman, N. H, and Shuster, L., eds. (Boston: 1998), pp. 283–304. Still other potential causes of CDS include, but are not limited to, elevated monoamine oxidase B activity and oxidation of central nervous system lipid membrane. See, e.g., Corey-Bloom, J., et al., *Monamine Oxidase Inhibitors in Neurological Diseases*, Lieberman, A., et al., eds. (New York: 1994), pp. 279–294; and Finnegan, K. T., *Monamine Oxidase Inhibitors in Neurological Diseases*, Lieberman, A., et al., eds. (New York: 1994), pp. 210–216.

Whatever the cause of COS, it can dramatically affect the health and well-being of an animal suffering from it. Further, the companionship offered by a cat or dog with CDS can become less rewarding as the severity of the disease increases and its symptoms, such as depression, anxiety, and/or generally decreased health, become more severe. A method for the treatment, control, and/or prevention of age-related behavioral disorders such as CDS is thus desirable.

SUMMARY OF THE INVENTION

This invention is directed to methods of treating age-related behavioral disorders in companion animals. The invention is further directed to methods of treating conditions associated with age-related behavioral disorders in companion animals.

A first embodiment of the invention encompasses a method of treating an age-related behavioral disorder in a companion animal comprising administering to a companion animal in need of such treatment a therapeutically effective amount of an acetylcholinesterase inhibitor. This embodiment encompasses methods of treating specific age-related behavioral disorders such as, but are not limited to, cognitive dysfunction syndrome and involutive depression.

A second embodiment of the invention encompasses a method of improving the cognitive processing of a companion animal comprising administering to a companion animal in need of such improvement an amount of an acetylcholinesterase inhibitor sufficient to improve cognitive processing.

A third embodiment of the invention encompasses a method of treating memory loss in a companion animal comprising administering to a companion animal in need of such treatment a therapeutically effective amount of an acetylcholinesterase inhibitor.

A fourth embodiment of the invention encompasses a method of treating disorientation or confusion in a companion animal comprising administering to a companion animal in need of such treatment a therapeutically effective amount of an acetylcholinesterase inhibitor.

A fifth embodiment of the invention encompasses a method of improving the social interactions of a companion animal comprising administering to a companion animal in need of such improvement a therapeutically effective amount of an acetylcholinesterase inhibitor.

A sixth embodiment of the invention encompasses a method of adjusting the sleep-wake cycle of a companion animal comprising administering to a companion animal in need of such adjustment a therapeutically effective amount of an acetylcholinesterase inhibitor.

A seventh embodiment of the invention encompasses a method of treating inappropriate elimination in a companion animal comprising administering to a companion animal in need of such treatment a therapeutically effective amount of an acetylcholinesterase inhibitor.

In preferred embodiments of the invention, the companion animal is a cat or dog. In preferred embodiments of the invention, the acetylcholinesterase inhibitor is a compound of Formula 1:

FORMULA I

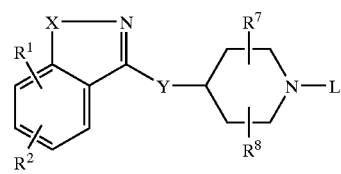

wherein $R^1$ and $R^2$ are each independently selected form the group consisting of hydrogen; ($C_1$–$C_6$) alkoxy; benzyloxy; phenoxy; hydroxy; phenyl; benzyl; halo; nitro; cyano; —$COR^5$; —$COOR^5$; —$CONHR^5$; —$NR^5R^6$; —$NR^5COR^6$; —$OCONR^5R^6$; —$NHCOOR^5$; ($C_1$–$C_6$) alkyl which may be substituted with from 1 to 3 fluorine atoms; $SO_p CH_2$-phenyl or $SO_p$($C_1$–$C_6$) alkyl, wherein p is 0, 1 or 2; pyridylmethyloxy or thienylmethyloxy; 2-oxazolyl; 2-thiazolyl; and benzenesulfonamide; wherein the phenyl moieties of said phenoxy, benzyloxy, phenyl, benzyl and benzenesulfonamide groups, the pyridyl and thienyl moieties of said pyridylmethyloxy or thienylmethyloxy groups, and the oxazolyl and thiazolyl moieties of said 2-oxazolyl and 2-thiazolyl groups may be substituted with 1 or 2 substituents independently selected from the group consisting of halo, $(C_1-C_4)$ alkyl, trifluoromethyl, $(C_1-C_4)$ alkoxy, cyano, nitro and hydroxy;

or $R^1$ and $R^2$ are attached to adjacent carbon atoms and form, together with the carbon atoms to which they are attached, a group of Formula 2:

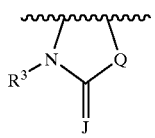

FORMULA 2 wherein $R^3$ is hydrogen or $(C_1-C_6)$ alkyl; J is oxygen, sulfur or $NR^4$; $R^4$ is hydrogen or $(C_1-C_4)$ alkyl; and Q is oxygen, sulfur, NH CHCH$_3$, $C(CH_3)_2$, —CH=CH—, or $(CH_2)_I$) wherein I is an integer from 1 to 3;

X is oxygen or sulfur;

Y is —$(CH_2)_m$—, —CH=CH$(CH_2)_n$—, or —O$(CH_2)_m$, wherein n is an integer from 0 to 3, and m is an integer from 1 to 3;

$R^5$ and $R^6$ are each independently selected from the group consisting of hydrogen, $(C_1-C_6)$ alkyl, phenyl, and benzyl, wherein the phenyl moieties of said phenyl and benzyl groups may be substituted with 1 or 2 substituents independently selected from the group consisting of fluoro, chloro, bromo, iodo, $(C_1-C_4)$ alkyl, trifluoromethyl, $(C_1-C_4)$ alkoxy, cyano, nitro and hydroxy; or $NR^5R^6$ together form a 4 or 5 membered ring wherein one atom of the ring is nitrogen and the other are carbon, oxygen or nitrogen; or $NR^5COR^6$ together form a 4- or 5-membered lactam ring;

L is phenyl, phenyl-$(C_1-C_6)$ alkyl, cinnamyl or pyridylmethyl, wherein the phenyl moieties of said phenyl and phenyl-$(C_1-C_6)$ alkyl may be substituted with 1 to 3 substituents independently selected from the group consisting of $(C_1-C_6)$ alkyl, $(C_1-C_6)$ alkoxy, $(C_1-C_4)$ alkoxycarbonyl, $(C_1-C_6)$ alkylcarbonyl, —OCONR$^5$R$^6$, —NHCOOR$^5$, and halo; or L is a group of Formula 3:

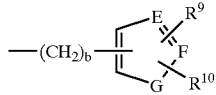

FORMULA 3 wherein b is an integer from 1 to 4; $R^9$ and $R^{10}$ are independently selected from the group consisting of hydrogen, $(C_1-C_4)$ alkyl, halo, and phenyl; E and F are independently —CH— or nitrogen; and G is oxygen, sulfur or $NR^4$, with the proviso that when E and F are both nitrogen, one of $R^9$ and $R^{10}$ is absent; and $R^7$ and $R^8$ are independently selected from the group consisting of hydrogen, $(C_1-C_6)$ alkyl, $(C_1-C_6)$ alkoxycarbonyl, $(C_1-C_6)$ alkylcarbonyl, and $(C_1-C_6)$ alkoxy, with the proviso that said $(C_1-C_6)$ alkoxy is not attached to a carbon that is adjacent to a nitrogen;

or a pharmaceutically acceptable salt or solvate thereof, and a pharmaceutically acceptable carrier.

In more preferred embodiments of the invention, the compound of Formula 1 is selected from the group consisting of:

5,7-dihydro-7-methyl-3-[2-[1-(phenylmethyl)-4-piperidinyl]ethyl]-6H-pyrrolo[4,5-f]-1,2-benzisoxazol-6-one;

5,7-dihydro-7-ethyl-3-[2[1-(phenylmethyl)-4-piperidinyl]ethyl]-6H-pyrrolo[4,5-f]-1,2-benzisoxazol-6-one;

5,7-dihydro-3-[2-[1-(2-chloro-5-thiophenemethyl)-4-piperidinyl]ethyl]6H-pyrrolo[4,5-f]-1,2-benzisoxazol-6-one;

5,7-dihydro-3-[2-[1-(2-methyl-4-thiazolemethyl)-4-piperidinyl]ethyl]-6H-pyrrolo[4,5-f]-1,2-benzisoxazol-6-one;

3-[2-[1-(3-bromophenylmethyl)-4-piperidinyl]ethyl]-5,7-dihydro-6H-pyrrolo[4,5-f]-1,2-benzisoxazol-6-one;

3-[2-[1-(4-bromophenylmethyl)-4-piperidinyl]ethyl]-5,7-dihydro-6H-pyrrolo[4,5-f]-1,2-benzisoxazol-6-one;

5,7-dihydro-3-[3-[1-(phenylmethyl)-4-piperidinyl] propyl]-6H-pyrrolo[4,5-f]-1,2-benzisoxazol-6-one;

6,8-dihydro-3-[2-[1-(phenylmethyl)-4-piperidinyl]ethyl]-7H-pyrrolo[5,4-g]-1,2-benzisoxazal-7-one; and 5,7-dihydro-3-[3-[1-(phenylmethyl)-4-piperidinyl]ethyl]-6H-pyrrolo[4,5-f]-1,2-benzisoxazol-6-one;

In most preferred embodiments of the invention, the compound of Formula I is 5,7-dihydro-3-[2-[1-(phenylmethyl)-4-piperidinyl]ethyl]-6H-pyrrolo[4,5-f]-1,2-benzisoxazol-6-one.

An eighth embodiment of the invention encompasses pharmaceutical compositions comprising a compound of Formula 1, or a pharmaceutically acceptable salt or solvate thereof, and a pharmaceutically acceptable carrier. Preferred compounds of Formula 1 are provided above. The pharmaceutical compositions of this invention are suitable for oral, rectal, parenteral (intravenous, intramuscular), transdermal, buccal, nasal, ocular, sublingual, topical, or subcutaneous administration. This embodiment further encompasses dosage forms of a compound of Formula 1, or a pharmaceutically acceptable salt or solvate thereof such as, but are not limited to, tablets, trochees, dispersions, suspensions, solutions, capsules, and patches. Preferred compounds of Formula 1 are provided above. The pharmaceutical compositions and dosage forms of the invention are particularly suited for the treatment of age-related behavioral disorders in companion animals.

Definitions

As used herein, the term "treating an age-related behavioral disorder" means treating, controlling, preventing and/or reducing one or more clinical signs (i.e., symptoms) of cognitive impairment observed in age-related behavioral disorders. Age-related disorders include, but are not limited to, cognitive dysfunction syndrome and involutive depression (also referred to as age-related cognitive and affective disorder). Symptoms of age-related behavioral disorders include, but are not limited to, the symptoms of cognitive dysfunction syndrome.

As used herein, the term "cognitive dysfunction syndrome" means the age-associated decline in the cognitive abilities of an animal that cannot be attributed to an unrelated general medical condition such as neoplasia, infection, or organ failure. Symptoms of cognitive dysfunction syndrome include, but are not limited to, memory loss, which may be manifested by disorientation and/or confusion, altered interaction with family members, changes in sleep-wake cycle, decreased activity level, and inappropriate elimination. The term further encompasses symptoms described by Ruehl, W. W., et al., *Psychopharmacology of Animal Behavior Disorders*, Dodman, N. H. and Shuster, L., eds., pp. 283–304 (Boston: 1988); Neilson, J. C., et al., JAVMA 210(8):1129–1134 (1997); Ruehl, W. W., et al., *Prog. Brain Res.* 106:217–225 (1995); and Ruehl, W. W., et al., *Adv. Pharmacol.* 42:316–319 (1998), all of which are incorporated herein by reference.

As used herein, the term "treating cognitive dysfunction syndrome" means reducing the severity of one or more symptoms associated with cognitive dysfunction syndrome.

As used herein, the term "treating involutive depression" means reducing the severity of one or more symptoms associated with involutive depression. Symptoms of involutive depression include, but are not limited to, depression, lethargy, and symptoms of cognitive dysfunction syndrome.

As used herein, the term "improving cognitive processing" means improving the ability of a companion animal to learn new tasks or to perform previously learned tasks.

As used herein, the term "treating memory loss" means improving the ability of a companion animal to, for example, remember objects, spatial relationships, people, or other animals, or to perform previously learned tasks.

As used herein, the term "treating disorientation or confusion" means diminishing the tendency of a companion animal to, for example, appear lost, to wander aimlessly, vocalize without cause, or to stare into space or at walls.

As used herein, the term "improving social interactions" means increasing the tendency of a patient to, for example, solicit the attention of family members or appropriately greet family members.

As used herein, the term "adjusting the sleep-wake cycle" means increasing the tendency of a patient to sleep at night, diminishing the tendency of a patient to sleep during the day, or diminishing the tendency of a patient to wander or pace during a 24-hour day.

As used herein, the terms "improving housetraining" and "treating inappropriate elimination" mean decreasing, for example, the frequency with which a companion animal urinates or defecates indoors, urinates or defecates indoors in view of family members, or urinates or defecates indoors shortly after being outdoors. For companion animals that would at one time signal to go outdoors, the terms encompass improving the frequency with which a companion animal signals to go outdoors.

As used herein, the term "a memory enhancing effective amount" means an amount of a compound that when administered to a companion animal increases the ability of the companion to remember objects, learned tasks, locations, people (e.g., family members), or other animals. A memory enhancing effective amount of a compound or mixture of compounds may be determined by one or more models known to those skilled in the art. Suitable models include, but are not limited to, those disclosed by Ruehl, W. W., et al., *Progress Brain Res.* Tipton, K. F., and Boulton, A. A., eds. (Elsevier Science: 1995), pp. 217–224; Head, E., et al., *Behavioral Neuroscience* 109:851–858 (1995): and Head, E., et al., *Prog. Neuro-Psychopharmacol. & Biol. Psychiatry* 20(5):15–530 (1996).

As used herein, the term "acetylcholinesterase inhibiting effective amount" means an amount of a compound that inhibits the in vivo or in vitro biological activity of acetylcholinesterase. The term encompasses the inhibition of acetylcholinesterase isolated from healthy animals as well as those exhibiting the symptoms of cognitive dysfunction syndrome. The term also encompasses the inhibition of acetylcholinesterase isolated from both brain and skeletal muscle.

As used herein, the term "pharmaceutically acceptable salt" means a non-toxic acid addition salt, i.e., a salt containing a pharmacologically acceptable anion such as, but not limited to, hydrochloride, hydrobromide, hydroiodide, nitrate, sulfate, bisulfate, phosphate, acid phosphate, acetate, lactate, citrate, acid citrate, tartrate, bitartrate, succinate, maleate, fumarate, gluconate, saccharate, benzoate, methanesulfonate, ethanesulfonate, benzenesulfonate, p-toluenesulfonate and pamoate (i.e., 1,1'-methylene-bis-(2-hydroxy-3-naphthoate)). A preferred pharmaceutically acceptable salt is maleate.

DETAILED DESCRIPTION OF THE INVENTION

This invention is based upon the discovery that acetylcholinesterase inhibitors can be effective in the treatment of age-related behavioral disorders in dogs and cats. Age-related behavioral disorders include, but are not limited to, cognitive dysfunction syndrome (CDS) and involutive depression. Preferred acetylcholinesterase inhibitors are those of Formula 1. Of these, icopezil, which is the maleate salt of 5,7-dihydro-3-[3-[1-(phenylmethyl)-4-piperidinyl]ethyl]-6H-pyrrolo[4,5-f]-1,2-benzisoxazol-6-one, is most preferred.

As mentioned above, the causes of age-related behavior disorders such as CDS are unknown. Unexpectedly, the inventors have discovered that age-related disorders can be treated by the administration of acetylcholinesterase inhibitors such as those of Formula 1. Without being limited by theory, it is now believed that CDS and related disorders can be treated by enhancing central cholinergic transmission and increasing the concentration of acetylcholine in the brain of an affected animal. It is further believed that cholinergic transmission can be enhanced by inhibiting the biological activity of acetylcholinesterase, a protein which catalyzes the breakdown of acetylcholine, thereby increasing the concentration of acetylcholine in the brain. The invention thus encompasses administering a memory enhancing effective amount, or an acetylcholinesterase inhibiting effective amount, of an acetylcholinesterase inhibitor to a patient (i.e., a companion animal) suffering from an age-related behavioral disorder.

The preparation of acetylcholinesterase inhibitors suitable for use in the methods and compositions of the invention is disclosed by: U.S. Pat. Nos. 5,750,542 and 5,538,984, and WO 92/17475, all of which are incorporated herein by reference. The abilities of these compounds to inhibit the activity of acetylcholinesterase can be determined by a variety of standard tests known to those skilled in the art. See, e.g., Mimori. Y., et al., *Behav. Brain Res.* 83:25–30 (1997); and Ellman, G. L., et al., *Biochem. Pharm.* 7:88–95 (1960). Their effectiveness in the treatment of age-related behavior disorders such as CDS can be determined by the methods described below, as well as by methods known to those skilled in the art. See, e.g., Ruehl, W. W., et al., *Progress Brain Res.* Tipton, K. F., and Boulton, A. A., eds. (Elsevier Science: 1995), pp. 217–224.

Pharmaceutical Formulations and Methods of Treatment

Compounds of Formula 1 and their pharmaceutically acceptable salts (hereinafter referred to as the "compounds of the invention") can be administered to a patient (i.e., a companion animal suffering from an age-related behavioral disorder such as CDS) by various methods. These include, but are not limited to, oral administration using capsules or tablets, parenteral administration using a sterile solution or suspension, and intravenous administration using a solution.

The free base compounds of the invention may be formulated and administered in the form of their pharmaceutically acceptable acid addition salts.

A preferred daily dose of the compounds of the invention is generally in the range of from about 0.001 to about 5 mg/kg/day, optionally from about 0.005 to about 1 mg/kg/day, and preferably from about 0.01 to about 0.50 mg/kg/day for the average companion animal, and may be administered in a single or divided doses. These dosages are encompassed by the phrases "therapeutically effective," "memory enhancing amount," "acetylcholinesterase inhibiting amount," and "sufficient to improve cognitive processing" as used herein.

When incorporated for parenteral administration into a solution or suspension, the compounds of the invention are present in a concentration of at least 1 weight percent, and preferably from about 4 to about 70 weight percent (based on the total weight of the unit). A typical parenteral dosage unit typically comprises from about 0.001 to about 100 mg of a compound of the invention.

The compounds of the invention can be administered orally with an inert diluent or an edible carrier, or may be enclosed in gelatine capsules or compressed into tablets. Such preparations typically contain at least 0.1% of a compound of the invention. A typical oral dosage unit contains from about 0.001 mg to about 100 mg of a compound of the invention.

The compounds of the invention can be administered alone or in combination with pharmaceutically acceptable carriers or diluents by the routes previously indicated. Such administration may be carried out in single or multiple doses. The compounds may be administered in a wide variety of different dosage forms, i.e., they may be combined with various pharmaceutically acceptable inert carriers in the form of tablets, capsules, lozenges, troches, powders, sprays, creams, salves, suppositories, jellies, gels, pastes, lotions, ointments, aqueous suspensions, injectable solutions, elixirs, syrups, and the like. Such carriers include solid diluents or fillers, sterile aqueous media and various non-toxic organic solvents. Moreover, oral pharmaceutical compositions can be suitably sweetened and/or flavored. In general, the compounds are present in such dosage forms at concentration levels ranging from about 5.0% to about 70% by weight.

For oral administration, tablets containing various excipients such as microcrystalline cellulose, sodium citrate, calcium carbonate, dicalcium phosphate and glycine may be employed along with various disintegrants such as starch (and preferably corn, potato or tapioca starch), alginic acid and certain complex silicates, together with granulation binders like polyvinylpyrrolidone, sucrose, gelatin and acacia. Lubricating agents, surfactants, and glidants such as magnesium stearate, sodium lauryl sulfate, and talc are also useful for tableting purposes. Solid compositions of a similar type may also be employed as fillers in gelatin capsules. Preferred fillers include lactose or milk sugar as well as high molecular weight polyethylene glycols. When aqueous suspensions and/or elixirs are desired for oral administration, the compound may be combined with various sweetening or flavoring agents, coloring matter or dyes, and, if so desired, emulsifying and/or suspending agents as well, together with diluents such as water, ethanol, propylene glycol, glycerin and various like combinations thereof.

In addition to the common dosage forms set out above, the compounds of the invention may be administered by controlled release means and/or delivery devices capable of releasing the compound at the required rate to maintain constant pharmacological activity for a desirable period of time. Such dosage forms provide a supply of a drug to the body during a predetermined period of time, and thus maintain drug levels in the therapeutic range for longer periods of time than conventional non-controlled formulations. Suitable controlled release pharmaceutical compositions and delivery devices that may be adapted for the administration of the compounds of the invention are described by U.S. Pat. Nos. 3,847,770; 3,916,899; 3,536,809; 3,598,123; 3,630,200; 4,008,719; 4,687,610; 4,769,027; 5,674,533; 5,059,595; 5,591,767; 5,120,548; 5,073,543; 5,639,476; 5,354,566; and 5,733,566, the disclosures of which are hereby incorporated by reference. For example, the compounds may be coupled to a class of biodegradable polymers useful in achieving controlled release of a drug, for example, polylactic acid, polyglycolic acid, copolymers of polylactic and polyglycolic acid, polyepsion caprolatone, polyhydroxy butyric acid, copolymers of polylactic and polyglycolic acid, polyepsilon caprolactone, polyhydroxy butyric acid, polyorthoesters, polyacetals, polydihydropyrans, polycyanoacrylates and cross-linked or amphipathic block copolymers of hydrogels.

Aqueous and non-aqueous solutions, and emulsions and mixtures thereof may be used for parenteral administration of the compounds of the invention. For example, a compound of the invention may be dissolved in an oil, such as sesame or peanut oil, in water, or in aqueous propylene glycol. Although not always necessary, aqueous solutions can be suitably buffered as is known in the art. Liquid diluents are preferably rendered isotonic prior to use. These aqueous solutions are suitable for intravenous injection purposes. The oily solutions are suitable for intraarticular, intramuscular and subcutaneous injection purposes. The preparation of all these solutions under sterile conditions is readily accomplished by standard pharmaceutical techniques well known to those skilled in the art.

It is also possible to administer the compounds of the invention topically. This may be done by way of creams, jellies, gels, pastes, patches, ointments and the like, in accordance with standard pharmaceutical practice. The compounds may further be administered in the feed of animals or orally as a drench composition.

The compounds may also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The compounds may also be coupled with soluble polymers as targetable drug carriers. Such polymers can include polyvinlpyrrolidone, pyran copolymer, polyhydroxypropyl-methacrylamide phenyl, polyhydroxyethylaspartamide-phenol, or polyethyleneoxide-polylysine substituted with palmitoyl residues.

Further novel aspects of the invention are described in the Examples which follow.

EXAMPLES

Example 1

Determination of CDS and the Effectiveness of its Treatment Using a Questionnaire One method of determining whether a dog suffers from CDS, and whether a dosage of a particular compound of the invention is effective in its treatment, utilizes a checklist designed to track a patient's behavioral changes over time. A suitable checklist is shown in Table 1.

TABLE 1

|  | Visit 1 | Visit 2 | Visit 3 | Visit 4 | Visit 5 | Visit 6 |
|---|---|---|---|---|---|---|
| DATE (month/day/year) |  |  |  |  |  |  |
| DISORIENTATION[1] |  |  |  |  |  |  |
| Wanders aimlessly |  |  |  |  |  |  |
| Appears lost or confused in house or yard |  |  |  |  |  |  |
| Gets "stuck" in corners or under/behind furniture |  |  |  |  |  |  |
| Stares into space or at walls |  |  |  |  |  |  |
| Has difficulty finding the door; stands at "hinge" side of door; stands at wrong door to go outside |  |  |  |  |  |  |
| Does not recognize familiar people |  |  |  |  |  |  |
| Does not respond to verbal cues or names |  |  |  |  |  |  |
| Appears to forget reason for going outdoors |  |  |  |  |  |  |
| ACTIVITY AND SLEEP |  |  |  |  |  |  |
| Sleeps more (overall) in a 24-hour day |  |  |  |  |  |  |
| Sleeps less during the night |  |  |  |  |  |  |
| Decrease in purposeful activity in a 24-hour day |  |  |  |  |  |  |
| Increase in aimless activity (wanders, paces) in a 24-hour day |  |  |  |  |  |  |
| HOUSETRAINING[2] |  |  |  |  |  |  |
| Urinates indoors (indicate # incidents per week) |  |  |  |  |  |  |
| Defecates indoors (# incidents per week) |  |  |  |  |  |  |
| Urinates or defecates indoors in view of owners |  |  |  |  |  |  |
| Urinates or defecates indoors soon after being outside |  |  |  |  |  |  |
| Signals less to go outside[3] |  |  |  |  |  |  |
| INTERACTION WITH FAMILY MEMBERS |  |  |  |  |  |  |
| Solicits attention less |  |  |  |  |  |  |
| Less likely to stand/lie for petting (walks away) |  |  |  |  |  |  |
| Less enthusiasm upon greeting |  |  |  |  |  |  |
| No longer greets owners (once dog is aware that owners have arrived) |  |  |  |  |  |  |

[1]The contribution of vision or hearing loss to behavior problems should be considered based upon chronicity; normal-aging (non-CDS) dogs tend to compensate for reduced vision or hearing.
[2]For dogs previously housetrained.
[3]For dogs who previously signaled (asked) to go outside.

If a dog greater than about seven years of age (or younger for giant breeds of dogs) shows signs in one or more categories, CDS should be considered, and a complete physical and neurological examination should be completed. Should the examination reveal no other causes for the symptoms exhibited by the patient, it can be supplemented, as appropriate, with diagnostic laboratory screening to identify other unrelated medical conditions that may be contributing to the clinical signs. If no unrelated medical condition is found, treatment with a compound of the invention may commence. A chart like that shown in Table 1 can then be used to determine the effectiveness of the treatment.

Example 2

Determination of CDS and the Effectiveness of its Treatment Using a Spatial Memory Model A between-subject design with a laboratory model for spatial memory may be used to quantify the effectiveness of the compounds of the invention in treating canine CDS. For example, the general effectiveness of icopezil can be tested in this way.

A suitable model is described by Head, E., et al., *Prog. Neuro-Psychopharmacol. & Biol. Psychiatry* 20(5):15–530 (1996). This model is sensitive to age-dependent cognitive impairment, and can be used to evaluate the ability of the compounds of the invention to enhance cognitive abilities. See also, Head, E., et al., *Behavioral Neuroscience* 109:851–858 (1995). According to this model, aged dogs show deficits in both acquisition and performance at long delays. Cognitively impaired aged dogs, for example, may perform within the range of normal dogs at short delays (e.g., 20 seconds), but not at longer delays. (e.g., 70–110 seconds). Performance of aged-impaired dogs on this test is improved by administration of selegiline chloride.

Other models known to those skilled in the art may also be adapted to test the effectiveness of the compounds of the invention in the treatment of both canine and feline CDS. Indeed, the present invention is not to be limited by the examples and details provided above, and its scope is further defined by the claims appended hereto.

What is claimed is:

1. A method of treating an age-related behavioral disorder in a companion animal comprising administering to a companion animal in need of such treatment a therapeutically effective amount of a compound of Formula I,

FORMULA I

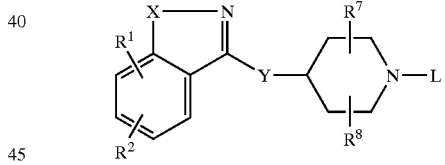

wherein $R^1$ and $R^2$ are each independently selected form the group consisting of hydrogen; ($C_1$–$C_6$) alkoxy; benzyloxy; phenoxy; hydroxy; phenyl; benzyl; halo; nitro; cyano; —$COR^5$; —$COOR^5$; —$CONHR^5$; —$NR^5R^6$; —$NR^5COR^6$; —$OCONR^5R^6$; —$NHCOOR^5$; ($C_1$–$C_6$) alkyl which may be substituted with from 1 to 3 fluorine atoms; $SO_pCH_2$-phenyl or $SO_p(C_1$–$C_6)$ alkyl, wherein p is 0, 1 or 2; pyridylmethyloxy or thienylmethyloxy; 2-oxazolyl; 2-thiazolyl; and benzenesulfonamide; wherein the phenyl moieties of said phenoxy, benzyloxy, phenyl, benzyl and benzenesulfonamide groups, the pyridyl and thienyl moieties of said pyridylmethyloxy or thienylmethyloxy groups, and the oxazolyl and thiazolyl moieties of said 2-oxazolyl and 2-thiazolyl groups may be substituted with 1 or 2 substituents independently selected from the group consisting of halo, ($C_1$–$C_4$) alkyl, trifluoromethyl, ($C_1$–$C_4$) alkoxy, cyano, nitro and hydroxy;

or $R^1$ and $R^2$ are attached to adjacent carbon atoms and form, together with the carbon atoms to which they are attached, a group of Formula 2:

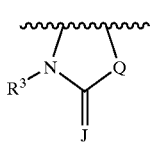

FORMULA 2 wherein $R^3$ is hydrogen or $(C_1-C_6)$ alkyl; J is oxygen, sulfur or $NR^4$; $R^4$ is hydrogen or $(C_1-C_4)$ alkyl; and Q is oxygen, sulfur, NH, $CHCH_3$, $C(CH_3)_2$, —CH=CH—, or $(CH_2)_I$ wherein I is an integer from 1 to 3;

X is oxygen or sulfur;

Y is —$(CH_2)_m$—, —$CH=CH(CH_2)_n$—, or —$O(CH_2)_m$—, wherein n is an integer from 0 to 3, and m is an integer from 1 to 3;

$R^5$ and $R^6$ are each independently selected from the group consisting of hydrogen, $(C_1-C_6)$ alkyl, phenyl, and benzyl, wherein the phenyl moieties of said phenyl and benzyl groups may be substituted with 1 or 2 substituents independently selected from the group consisting of fluoro, chloro, bromo, iodo, $(C_1-C_4)$ alkyl, trifluoromethyl, $(C_1-C_4)$ alkoxy, cyano, nitro and hydroxy; or $NR^5R^6$ together form a 4 or 5 membered ring wherein one atom of the ring is nitrogen and the other is carbon, oxygen or nitrogen; or $NR^5COR^6$ together form a 4- or 5-membered lactam ring;

L is phenyl, phenyl-$(C_1-C_6)$ alkyl, cinnamyl or pyridylmethyl, wherein the phenyl moieties of said phenyl and phenyl-$(C_1-C_6)$ alkyl may be substituted with 1 to 3 substituents independently selected from the group consisting of $(C_1-C_6)$ alkyl, $(C_1-C_6)$ alkoxy, $(C_1-C_4)$ alkoxycarbonyl, $(C_1-C_6)$ alkylcarbonyl, —$OCONR^5R^6$, —$NHCOOR^5$, and halo; or L is a group of Formula 3:

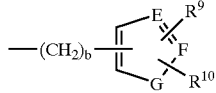

FORMULA 3 wherein b is an integer from 1 to 4; $R^9$ and $R^{10}$ are independently selected from the group consisting of hydrogen, $(C_1-C_4)$ alkyl, halo, and phenyl; E and F are independently —CH— or nitrogen; and G is oxygen, sulfur or $NR^4$, with the proviso that when E and F are both nitrogen, one of $R^9$ and $R^{10}$ is absent; and $R^7$ and $R^8$ are independently selected from the group consisting of hydrogen, $(C_1-C_6)$ alkyl, $(C_1-C_6)$ alkoxycarbonyl, $(C_1-C_6)$ alkylcarbonyl, and $(C_1-C_6)$ alkoxy, with the proviso that said $(C_1-C_6)$ alkoxy is not attached to a carbon that is adjacent to a nitrogen;

or a pharmaceutically acceptable salt or solvate thereof, and a pharmaceutically acceptable carrier.

2. The method of claim 1 wherein the age-related behavioral disorder is cognitive dysfunction syndrome or involutive depression.

3. The method of claim 1 wherein the compound of Formula I is selected from the group consisting of:

5,7-dihydro-7-methyl-3-[2-[1-(phenylmethyl)-4-piperidinyl]ethyl]-6H-pyrrolo[4,5-f]-1,2-benzisoxazol-6-one;

5,7-dihydro-7-ethyl-3-[2-[1-(phenylmethyl)-4-piperidinyl]ethyl]-6H-pyrrolo[4,5-f]-1,2-benzisoxazol-6-one;

5,7-dihydro-3-[2-[1-(2-chloro-5-thiophenemethyl)-4-piperidinyl]ethyl]-6H-pyrrolo[4,5-f]-1,2-benzisoxazol-6-one;

5,7-dihydro-3-[2-[1-(2-methyl-4-thiazolemethyl)-4-piperidinyl]ethyl]-6H-pyrrolo[4,5-f]-1,2-benzisoxazol-6-one;

3-[2-[1-(3-bromophenylmethyl)-4-piperidinyl]ethyl]-5,7-dihydro-6H-pyrrolo[4,5-f]-1,2-benzisoxazol-6-one;

3-[2-[1-(4-bromophenylmethyl)-4-piperidinyl]ethyl]-5,7-dihydro-6H-pyrrolo[4,5-f]-1,2-benzisoxazol-6-one;

5,7-dihydro-3-[3-[1-(phenylmethyl)-4-piperidinyl]propyl]-6H-pyrrolo[4,5-f]-1,2-benzisoxazol-6-one;

6,8-dihydro-3-[2-[1-(phenylmethyl)-4-piperidinyl]ethyl]-7H-pyrrolo[5,4-g]-1,2-benzisoxazol-7-one; and 5,7-dihydro-3-[2-(1-(phenylmethyl)-4-piperidinyl]ethyl]-6H-pyrrolo[4,5-f]-1,2-benzisoxazol-6-one.

4. The method of claim 3 wherein the compound of Formula I is 5,7-dihydro-3-[2-(1-(phenylmethyl)-4-piperidinyl]ethyl]-6H-pyrrolo[4,5-f]-1,2-benzisoxazol-6-one.

5. A dosage form of a compound of claim 1 for use in the treatment of an age-related behavioral disorder in a companion animal.

6. The dosage form of claim 5 wherein said dosage form is a tablet, troche, dispersion, suspension, solution, capsule, or patch.

7. The dosage form of claim 6 wherein the compound of claim 1 is selected from the group consisting of:

5,7-dihydro-7-methyl-3-[2-[1-(phenylmethyl)-4-piperidinyl]ethyl]-6H-pyrrolo[4,5-f]-1,2-benzisoxazol-6-one;

5,7-dihydro-7-ethyl-3-[2-[1-(phenylmethyl)-4-piperidinyl]ethyl]-6H-pyrrolo[4,5-f]-1,2-benzisoxazol-6-one;

5,7-dihydro-3-[2-[1-(2-chloro-5-thiophenemethyl)-4-piperidinyl]ethyl]-6H-pyrrolo[4,5-f]-1,2-benzisoxazol-6-one;

5,7-dihydro-3-[2-[1-(2-methyl-4-thiazolemethyl)-4-piperidinyl]ethyl]-6H-pyrrolo[4,5-f]-1,2-benzisoxazol-6-one;

3-[2-[1-(3-bromophenylmethyl)-4-piperidinyl]ethyl]-5,7-dihydro-6H-pyrrolo[4,5-f]-1,2-benzisoxazol-6-one;

3-[2-[1-(4-bromophenylmethyl)-4-piperidinyl]ethyl]-5,7-dihydro-6H-pyrrolo[4,5-f]-1,2-benzisoxazol-6-one;

5,7-dihydro-3-[3-[1-(phenylmethyl)-4-piperidinyl]propyl]-6H-pyrrolo[4,5-f]-1,2-benzisoxazol-6-one;

6,8-dihydro-3-[2-[1-(phenylmethyl)-4-piperidinyl]ethyl]-7H-pyrrolo[5,4-g]-1,2-benzisoxazol-7-one; and 5,7-dihydro-3-[2-(1-phenylmethyl)-4-piperidinyl]ethyl]-6H-pyrrolo[4,5-f]-1,2-benzisoxazol-6-one.

8. The dosage form of claim 7 wherein the compound of Formula 1 is 5,7-dihydro-3-[2-1[phenylmethyl)-4-piperidinyl]ethyl]-6H-pyrrolo[4,5-f]-1,2-benzisoxazol-6-one.

9. The dosage form of claim 8 wherein said dosage form comprises from about 0.001 mg to about 100 mg of the compound of claim 1.

10. A method of improving the cognitive processing of a companion animal comprising administering to a compan ion animal in need of such treatment a therapeutically effective amount of a compound of Formula I,

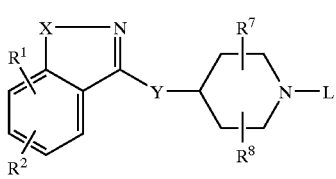

FORMULA I wherein $R^1$ and $R^2$ are each independently selected form the group consisting of hydrogen; $(C_1–C_6)$ alkoxy; benzyloxy; phenoxy; hydroxy; phenyl; benzyl; halo; nitro; cyano; —$COR^5$; —$COOR^5$; —$CONHR^5$; —$NR^5R^6$; —$NR^5COR^6$; —$OCONR^5R^6$; —$NHCOOR^5$; $(C_1–C_6)$ alkyl which may be substituted with from 1 to 3 fluorine atoms; $SO_pCH_2$-phenyl or $SO_p(C_1–C_6)$ alkyl, wherein p is 0, 1 or 2; pyridylmethyloxy or thienylmethyloxy; 2-oxazolyl; 2-thiazolyl; and benzenesulfonamide; wherein the phenyl moieties of said phenoxy, benzyloxy, phenyl, benzyl and benzenesulfonamide groups, the pyridyl and thienyl moieties of said pyridylmethyloxy or thienylmethyloxy groups, and the oxazolyl and thiazolyl moieties of said 2-oxazolyl and 2-thiazolyl groups may be substituted with 1 or 2 substituents independently selected from the group consisting of halo, $(C_1–C_4)$ alkyl, trifluoromethyl, $(C_1–C_4)$ alkoxy, cyano, nitro and hydroxy;

or $R^1$ and $R^2$ are attached to adjacent carbon atoms and form, together with the carbon atoms to which they are attached, a group of Formula 2:

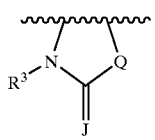

FORMULA 2 wherein $R^3$ is hydrogen or $(C_1–C_6)$ alkyl; J is oxygen, sulfur or $NR^4$; $R^4$ is hydrogen or $(C_1–C_4)$ alkyl; and Q is oxygen, sulfur, NH, $CHCH_3$, $C(CH_3)_2$, —CH=CH—, or $(CH_2)_I$ wherein I is an integer from 1 to 3;

X is oxygen or sulfur;

Y is —$(CH_2)_m$—, —$CH=CH(CH_2)_n$—, or —$O(CH_2)_m$—, wherein n is an integer from 0 to 3, and m is an integer from 1 to 3;

$R^5$ and $R^6$ are each independently selected from the group consisting of hydrogen, $(C_1–C_6)$ alkyl, phenyl, and benzyl, wherein the phenyl moieties of said phenyl and benzyl groups may be substituted with 1 or 2 substituents independently selected from the group consisting of fluoro, chloro, bromo, iodo, $(C_1–C_4)$ alkyl, trifluoromethyl, $(C_1–C_4)$ alkoxy, cyano, nitro and hydroxy; or $NR^5R^6$ together form a 4 or 5 membered ring wherein one atom of the ring is nitrogen and the other is carbon, oxygen or nitrogen; or $NR^5COR^6$ together form a 4- or 5-membered lactam ring;

L is phenyl, phenyl-$(C_1–C_6)$ alkyl, cinnamyl or pyridylmethyl, wherein the phenyl moieties of said phenyl and phenyl-$(C_1–C_6)$ alkyl may be substituted with 1 to 3 substituents independently selected from the group consisting of $(C_1–C_6)$ alkyl, $(C_1–C_6)$ alkoxy, $(C_1–C_4)$ alkoxycarbonyl, $(C_1–C_6)$ alkylcarbonyl, —$OCONR^5R^6$, —$NHCOOR^5$, and halo; or L is a group of Formula 3:

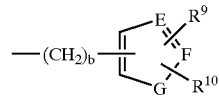

FORMULA 3 wherein b is an integer from 1 to 4; $R^9$ and $R^{10}$ are independently selected from the group consisting of hydrogen, $(C_1–C_4)$ alkyl, halo, and phenyl; E and F are independently —CH— or nitrogen; and G is oxygen, sulfur or $NR^4$, with the proviso that when E and F are both nitrogen, one of $R^9$ and $R^{10}$ is absent; and $R^7$ and $R^8$ are independently selected from the group consisting of hydrogen, $(C_1–C_6)$ alkyl, $(C_1–C_6)$ alkoxycarbonyl, $(C_1–C_6)$ alkylcarbonyl, and $(C_1–C_6)$ alkoxy, with the proviso that said $(C_1–C_6)$ alkoxy is not attached to a carbon that is adjacent to a nitrogen;

or a pharmaceutically acceptable salt or solvate thereof, and a pharmaceutically acceptable carrier.

11. A method of treating memory loss in a companion animal comprising administering to a companion animal in need of such treatment a therapeutically effective amount of a compound of Formula I,

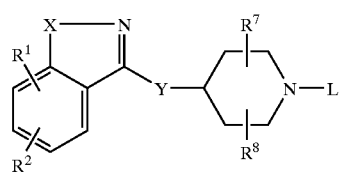

FORMULA I wherein $R^1$ and $R^2$ are each independently selected form the group consisting of hydrogen; $(C_1–C_6)$ alkoxy; benzyloxy; phenoxy; hydroxy; phenyl; benzyl; halo; nitro; cyano; —$COR^5$; —$COOR^5$; —$CONHR^5$; —$NR^5R^6$; —$NR^5COR^6$; —$OCONR^5R^6$; —$NHCOOR^5$; $(C_1–C_6)$ alkyl which may be substituted with from 1 to 3 fluorine atoms; $SO_pCH_2$-phenyl or $SO_p(C_1–C_6)$ alkyl, wherein p is 0, 1 or 2; pyridylmethyloxy or thienylmethyloxy; 2-oxazolyl; 2-thiazolyl; and benzenesulfonamide; wherein the phenyl moieties of said phenoxy, benzyloxy, phenyl, benzyl and benzenesulfonamide groups, the pyridyl and thienyl moieties of said pyridylmethyloxy or thienylmethyloxy groups, and the oxazolyl and thiazolyl moieties of said 2-oxazolyl and 2-thiazolyl groups may be substituted with 1 or 2 substituents independently selected from the group consisting of halo, $(C_1–C_4)$ alkyl, trifluoromethyl, $(C_1–C_4)$ alkoxy, cyano, nitro and hydroxy;

or $R^1$ and $R^2$ are attached to adjacent carbon atoms and form, together with the carbon atoms to which they are attached, a group of Formula 2:

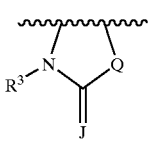

FORMULA 2 wherein $R^3$ is hydrogen or $(C_1–C_6)$ alkyl; J is oxygen, sulfur or $NR^4$; $R^4$ is hydrogen or $(C_1–C_4)$ alkyl; and Q is oxygen, sulfur, NH, CHCH$_3$, C(CH$_3$)$_2$, —CH=CH—, or (CH$_2$)$_I$ wherein I is an integer from 1 to 3;

X is oxygen or sulfur;

Y is —(CH$_2$)$_m$—, —CH=CH(CH$_2$)$_n$—, or —O(CH$_2$)$_m$—, wherein n is an integer from 0 to 3, and m is an integer from 1 to 3;

R$^5$ and R$^6$ are each independently selected from the group consisting of hydrogen, (C$_1$–C$_6$) alkyl, phenyl, and benzyl, wherein the phenyl moieties of said phenyl and benzyl groups may be substituted with 1 or 2 substituents independently selected from the group consisting of fluoro, chloro, bromo, iodo, (C$_1$–C$_4$) alkyl, trifluoromethyl, (C$_1$–C$_4$) alkoxy, cyano, nitro and hydroxy; or NR$^5$R$^6$ together form a 4 or 5 membered ring wherein one atom of the ring is nitrogen and the other is carbon, oxygen or nitrogen; or NR$^5$COR$^6$ together form a 4- or 5-membered lactam ring;

L is phenyl, phenyl-(C$_1$–C$_6$) alkyl, cinnamyl or pyridylmethyl, wherein the phenyl moieties of said phenyl and phenyl-(C$_1$–C$_6$) alkyl may be substituted with 1 to 3 substituents independently selected from the group consisting of (C$_1$–C$_6$) alkyl, (C$_1$–C$_6$) alkoxy, (C$_1$–C$_4$) alkoxycarbonyl, (C$_1$–C$_6$) alkylcarbonyl, —OCONR$^5$R$^6$, —NHCOOR$^5$, and halo; or L is a group of Formula 3:

FORMULA 3

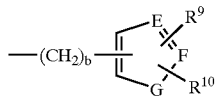

wherein b is an integer from 1 to 4; R$^9$ and R$^{10}$ are independently selected from the group consisting of hydrogen, (C$_1$–C$_4$) alkyl, halo, and phenyl; E and F are independently —CH— or nitrogen; and G is oxygen, sulfur or NR$^4$, with the proviso that when E and F are both nitrogen, one of R$^9$ and R$^{10}$ is absent; and R$^7$ and R$^8$ are independently selected from the group consisting of hydrogen, (C$_1$–C$_6$) alkyl, (C$_1$–C$_6$) alkoxycarbonyl, (C$_1$–C$_6$) alkylcarbonyl, and (C$_1$–C$_6$) alkoxy, with the proviso that said (C$_1$–C$_6$) alkoxy is not attached to a carbon that is adjacent to a nitrogen;

or a pharmaceutically acceptable salt or solvate thereof, and a pharmaceutically acceptable carrier.

12. A method of treating disorientation or confusion in a companion animal comprising administering to a companion animal in need of such treatment a therapeutically effective amount of a compound of Formula I,

FORMULA I

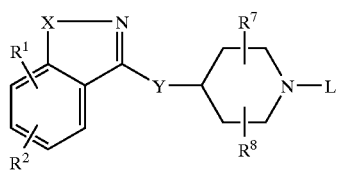

wherein R$^1$ and R$^2$ are each independently selected form the group consisting of hydrogen; (C$_1$–C$_6$) alkoxy; benzyloxy; phenoxy; hydroxy; phenyl; benzyl; halo; nitro; cyano; —COR$^5$; —COOR$^5$; —CONHR$^5$; —NR$^5$R$^6$; —NR$^5$COR$^6$; —OCONR$^5$R$^6$; —NHCOOR$^5$; (C$_1$–C$_6$) alkyl which may be substituted with from 1 to 3 fluorine atoms; SO$_p$CH$_2$-phenyl or SO$_p$(C$_1$–C$_6$) alkyl, wherein p is 0, 1 or 2; pyridylmethyloxy or thienylmethyloxy; 2-oxazolyl; 2-thiazolyl; and benzenesulfonamide; wherein the phenyl moieties of said phenoxy, benzyloxy, phenyl, benzyl and benzenesulfonamide groups, the pyridyl and thienyl moieties of said pyridylmethyloxy or thienylmethyloxy groups, and the oxazolyl and thiazolyl moieties of said 2-oxazolyl and 2-thiazolyl groups may be substituted with 1 or 2 substituents independently selected from the group consisting of halo, (C$_1$–C$_4$) alkyl, trifluoromethyl, (C$_1$–C$_4$) alkoxy, cyano, nitro and hydroxy;

or R$^1$ and R$^2$ are attached to adjacent carbon atoms and form, together with the carbon atoms to which they are attached, a group of Formula 2:

FORMULA 2

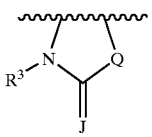

wherein R$^3$ is hydrogen or (C$_1$–C$_6$) alkyl; J is oxygen, sulfur or NR$^4$; R$^4$ is hydrogen or (C$_1$–C$_4$) alkyl; and Q is oxygen, sulfur, NH, CHCH$_3$, C(CH$_3$)$_2$, —CH=CH—, or (CH$_2$)$_I$ wherein I is an integer from 1 to 3;

X is oxygen or sulfur;

Y is —(CH$_2$)$_m$—, —CH=CH(CH$_2$)$_n$—, or —O(CH$_2$)$_m$—, wherein n is an integer from 0 to 3, and m is an integer from 1 to 3;

R$^5$ and R$^6$ are each independently selected from the group consisting of hydrogen, (C$_1$–C$_6$) alkyl, phenyl, and benzyl, wherein the phenyl moieties of said phenyl and benzyl groups may be substituted with 1 or 2 substituents independently selected from the group consisting of fluoro, chloro, bromo, iodo, (C$_1$–C$_4$) alkyl, trifluoromethyl, (C$_1$–C$_4$) alkoxy, cyano, nitro and hydroxy; or NR$^5$R$^6$ together form a 4 or 5 membered ring wherein one atom of the ring is nitrogen and the other is carbon, oxygen or nitrogen; or NR$^5$COR$^6$ together form a 4- or 5-membered lactam ring;

L is phenyl, phenyl-(C$_1$–C$_6$) alkyl, cinnamyl or pyridylmethyl, wherein the phenyl moieties of said phenyl and phenyl-(C$_1$–C$_6$) alkyl may be substituted with 1 to 3 substituents independently selected from the group consisting of (C$_1$–C$_6$) alkyl, (C$_1$–C$_6$) alkoxy, (C$_1$–C$_4$) alkoxycarbonyl, (C$_1$–C$_6$) alkylcarbonyl, —OCONR$^5$R$^6$, —NHCOOR$^5$, and halo; or L is a group of Formula 3:

FORMULA 3

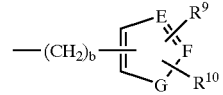

wherein b is an integer from 1 to 4; R$^9$ and R$^{10}$ are independently selected from the group consisting of hydrogen, (C$_1$–C$_4$) alkyl, halo, and phenyl; E and F are independently —CH— or nitrogen; and G is oxygen, sulfur or NR$^4$, with the proviso that when E and F are both nitrogen, one of R$^9$ and R$^{10}$ is absent; and R$^7$ and R$^8$ are independently selected from the group consisting of hydrogen, (C$_1$–C$_6$) alkyl, (C$_1$–C$_6$) alkoxycarbonyl, (C$_1$–C$_6$) alkylcarbonyl, and (C$_1$–C$_6$) alkoxy, with the proviso that said (C$_1$–C$_6$) alkoxy is not attached to a carbon that is adjacent to a nitrogen;

or a pharmaceutically acceptable salt or solvate thereof, and a pharmaceutically acceptable carrier.

13. A method of improving social interactions of a companion animal comprising administering to a companion animal in need of such treatment a therapeutically effective amount of a compound of Formula I,

FORMULA I

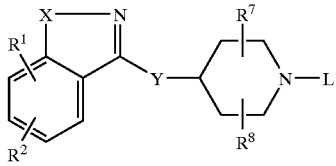

wherein $R^1$ and $R^2$ are each independently selected form the group consisting of hydrogen; ($C_1$–$C_6$) alkoxy; benzyloxy; phenoxy; hydroxy; phenyl; benzyl; halo; nitro; cyano; —$COR^5$; —$COOR^5$; —$CONHR^5$; —$NR^5R^6$; —$NR^5COR^6$; —$OCONR^5R^6$; —$NHCOOR^5$; ($C_1$–$C_6$) alkyl which may be substituted with from 1 to 3 fluorine atoms; $SO_p CH_2$-phenyl or $SO_p$($C_1$–$C_6$) alkyl, wherein p is 0, 1 or 2; pyridylmethyloxy or thienylmethyloxy; 2-oxazolyl; 2-thiazolyl; and benzenesulfonamide; wherein the phenyl moieties of said phenoxy, benzyloxy, phenyl, benzyl and benzenesulfonamide groups, the pyridyl and thienyl moieties of said pyridylmethyloxy or thienylmethyloxy groups, and the oxazolyl and thiazolyl moieties of said 2-oxazolyl and 2-thiazolyl groups may be substituted with 1 or 2 substituents independently selected from the group consisting of halo, ($C_1$–$C_4$) alkyl, trifluoromethyl, ($C_1$–$C_4$) alkoxy, cyano, nitro and hydroxy;

or $R^1$ and $R^2$ are attached to adjacent carbon atoms and form, together with the carbon atoms to which they are attached, a group of Formula 2:

FORMULA 2

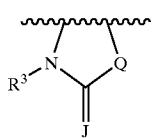

wherein $R^3$ is hydrogen or ($C_1$–$C_6$) alkyl; J is oxygen, sulfur or $NR^4$; $R^4$ is hydrogen or ($C_1$–$C_4$) alkyl; and Q is oxygen, sulfur, NH, $CHCH_3$, $C(CH_3)_2$, —CH=CH—, or $(CH_2)_I$ wherein I is an integer from 1 to 3;

X is oxygen or sulfur;

Y is —$(CH_2)_m$—, —CH=CH$(CH_2)_n$—, or —O$(CH_2)_m$—, wherein n is an integer from 0 to 3, and m is an integer from 1 to 3;

$R^5$ and $R^6$ are each independently selected from the group consisting of hydrogen, ($C_1$–$C_6$) alkyl, phenyl, and benzyl, wherein the phenyl moieties of said phenyl and benzyl groups may be substituted with 1 or 2 substituents independently selected from the group consisting of fluoro, chloro, bromo, iodo, ($C_1$–$C_4$) alkyl, trifluoromethyl, ($C_1$–$C_4$) alkoxy, cyano, nitro and hydroxy; or $NR^5R^6$ together form a 4 or 5 membered ring wherein one atom of the ring is nitrogen and the other is carbon, oxygen or nitrogen; or $NR^5COR^6$ together form a 4- or 5-membered lactam ring;

L is phenyl, phenyl-($C_1$–$C_6$) alkyl, cinnamyl or pyridylmethyl, wherein the phenyl moieties of said phenyl and phenyl-($C_1$–$C_6$) alkyl may be substituted with 1 to 3 substituents independently selected from the group consisting of ($C_1$–$C_6$) alkyl, ($C_1$–$C_6$) alkoxy, ($C_1$–$C_4$) alkoxycarbonyl, ($C_1$–$C_6$) alkylcarbonyl, —$OCONR^5R^6$, —$NHCOOR^5$, and halo; or L is a group of Formula 3:

FORMULA 3

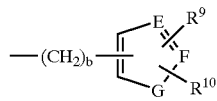

wherein b is an integer from 1 to 4; $R^9$ and $R^{10}$ are independently selected from the group consisting of hydrogen, ($C_1$–$C_4$) alkyl, halo, and phenyl; E and F are independently —CH— or nitrogen; and G is oxygen, sulfur or $NR^4$, with the proviso that when E and F are both nitrogen, one of $R^9$ and $R^{10}$ is absent; and $R^7$ and $R^8$ are independently selected from the group consisting of hydrogen, ($C_1$–$C_6$) alkyl, ($C_1$–$C_6$) alkoxycarbonyl, ($C_1$–$C_6$) alkylcarbonyl, and ($C_1$–$C_6$) alkoxy, with the proviso that said ($C_1$–$C_6$) alkoxy is not attached to a carbon that is adjacent to a nitrogen;

or a pharmaceutically acceptable salt or solvate thereof, and a pharmaceutically acceptable carrier.

14. A method of adjusting the sleep-wake cycle of a companion animal comprising administering to a companion animal in need of such treatment a therapeutically effective amount of a compound of Formula I,

FORMULA I

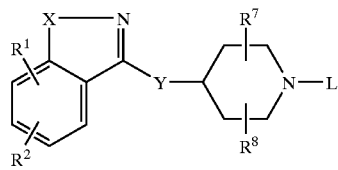

wherein $R^1$ and $R^2$ are each independently selected form the group consisting of hydrogen; ($C_1$–$C_6$) alkoxy, benzyloxy; phenoxy; hydroxy; phenyl; benzyl; halo; nitro; cyano; —$COR^5$; —$COOR^5$; —$CONHR^5$; —$NR^5R^6$; —$NR^5COR^6$; —$OCONR^5R^6$; —$NHCOOR^5$; ($C_1$–$C_6$) alkyl which may be substituted with from 1 to 3 fluorine atoms; $SO_p CH_2$-phenyl or $SO_p$($C_1$–$C_6$) alkyl, wherein p is 0, 1 or 2; pyridylmethyloxy or thienylmethyloxy, 2-oxazolyl; 2-thiazolyl; and benzenesulfonamide; wherein the phenyl moieties of said phenoxy, benzyloxy, phenyl, benzyl and benzenesulfonamide groups, the pyridyl and thienyl moieties of said pyridylmethyloxy or thienylmethyloxy groups, and the oxazolyl and thiazolyl moieties of said 2-oxazolyl and 2-thiazolyl groups may be substituted with 1 or 2 substituents independently selected from the group consisting of halo, ($C_1$–$C_4$) alkyl, trifluoromethyl, ($C_1$–$C_4$) alkoxy, cyano, nitro and hydroxy;

or $R^1$ and $R^2$ are attached to adjacent carbon atoms and form, together with the carbon atoms to which they are attached, a group of Formula 2:

FORMULA 2

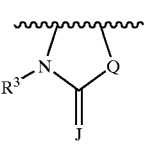

wherein $R^3$ is hydrogen or ($C_1$–$C_6$) alkyl; J is oxygen, sulfur or $NR^4$; $R^4$ is hydrogen or ($C_1$–$C_4$) alkyl; and Q is oxygen, sulfur, NH, CHCH$_3$, C(CH$_3$)$_2$, —CH=CH—, or (CH$_2$)$_I$ wherein I is an integer from 1 to 3;

X is oxygen or sulfur;

Y is —(CH$_2$)$_m$—, —CH=CH(CH$_2$)$_n$—, or —O(CH$_2$)$_m$—, wherein n is an integer from 0 to 3, and m is an integer from 1 to 3;

R$^5$ and R$^6$ are each independently selected from the group consisting of hydrogen, (C$_1$–C$_6$) alkyl, phenyl, and benzyl, wherein the phenyl moieties of said phenyl and benzyl groups may be substituted with 1 or 2 substituents independently selected from the group consisting of fluoro, chloro, bromo, iodo, (C$_1$–C$_4$) alkyl, trifluoromethyl, (C$_1$–C$_4$) alkoxy, cyano, nitro and hydroxy; or NR$^5$R$^6$ together form a 4 or 5 membered ring wherein one atom of the ring is nitrogen and the other is carbon, oxygen or nitrogen; or NR$^5$COR$^6$ together form a 4- or 5-membered lactam ring;

L is phenyl, phenyl-(C$_1$–C$_6$) alkyl, cinnamyl or pyridylmethyl, wherein the phenyl moieties of said phenyl and phenyl-(C$_1$–C$_6$) alkyl may be substituted with 1 to 3 substituents independently selected from the group consisting of (C$_1$–C$_6$) alkyl, (C$_1$–C$_6$) alkoxy, (C$_1$–C$_4$) alkoxycarbonyl, (C$_1$–C$_6$) alkylcarbonyl, —OCONR$^5$R$^6$, —NHCOOR$^5$, and halo; or L is a group of Formula 3:

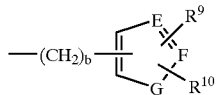

FORMULA 3 wherein b is an integer from 1 to 4; R$^9$ and R$^{10}$ are independently selected from the group consisting of hydrogen, (C$_1$–C$_4$) alkyl, halo, and phenyl; E and F are independently —CH— or nitrogen; and G is oxygen, sulfur or NR$^4$, with the proviso that when E and F are both nitrogen, one of R$^9$ and R$^{10}$ is absent; and R$^7$ and R$^8$ are independently selected from the group consisting of hydrogen, (C$_1$–C$_6$) alkyl, (C$_1$–C$_6$) alkoxycarbonyl, (C$_1$–C$_6$) alkylcarbonyl, and (C$_1$–C$_6$) alkoxy, with the proviso that said (C$_1$–C$_6$) alkoxy is not attached to a carbon that is adjacent to a nitrogen;

or a pharmaceutically acceptable salt or solvate thereof, and a pharmaceutically acceptable carrier.

15. A method of treating inappropriate elimination in a companion animal comprising administering to a companion animal in need of such treatment a therapeutically effective amount of a compound of Formula I,

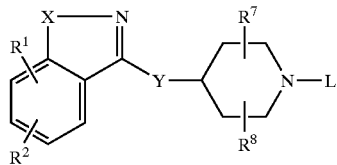

FORMULA I wherein R$^1$ and R$^2$ are each independently selected form the group consisting of hydrogen; (C$_1$–C$_6$) alkoxy; benzyloxy; phenoxy; hydroxy; phenyl; benzyl; halo; nitro; cyano; —COR$^5$; —COOR$^5$; —CONHR$^5$; —NR$^5$R$^6$; —NR$^5$COR$^6$; —OCONR$^5$R$^6$; —NHCOOR$^5$; (C$_1$–C$_6$) alkyl which may be substituted with from 1 to 3 fluorine atoms; SO$_p$CH$_2$-phenyl or SO$_p$(C$_1$–C$_6$) alkyl, wherein p is 0, 1 or 2; pyridylmethyloxy or thienylmethyloxy, 2-oxazolyl; 2-thiazolyl; and benzenesulfonamide; wherein the phenyl moieties of said phenoxy, benzyloxy, phenyl, benzyl and benzenesulfonamide groups, the pyridyl and thienyl moieties of said pyridylmethyloxy or thienylmethyloxy groups, and the oxazolyl and thiazolyl moieties of said 2-oxazolyl and 2-thiazolyl groups may be substituted with 1 or 2 substituents independently selected from the group consisting of halo, (C$_1$–C$_4$) alkyl, trifluoromethyl, (C$_1$–C$_4$) alkoxy, cyano, nitro and hydroxy;

or R$^1$ and R$^2$ are attached to adjacent carbon atoms and form, together with the carbon atoms to which they are attached, a group of Formula 2:

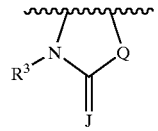

FORMULA 2 wherein R$^3$ is hydrogen or (C$_1$–C$_6$) alkyl; J is oxygen, sulfur or NR$^4$; R$^4$ is hydrogen or (C$_1$–C$_4$) alkyl; and Q is oxygen, sulfur, NH, CHCH$_3$, C(CH$_3$)$_2$, —CH=CH—, or (CH$_2$)$_I$ wherein I is an integer from 1 to 3;

X is oxygen or sulfur;

Y is CH$_2$)$_m$—, —CH=CH(CH$_2$)$_n$—, or —O(CH$_2$)$_m$—, wherein n is an integer from 0 to 3, and m is an integer from 1 to 3;

R$^5$ and R$^6$ are each independently selected from the group consisting of hydrogen, (C$_1$–C$_6$) alkyl, phenyl, and benzyl, wherein the phenyl moieties of said phenyl and benzyl groups may be substituted with 1 or 2 substituents independently selected from the group consisting of fluoro, chloro, bromo, iodo, (C$_1$–C$_4$) alkyl, trifluoromethyl, (C$_1$–C$_4$) alkoxy, cyano, nitro and hydroxy; or NR$^5$R$^6$ together form a 4 or 5 membered ring wherein one atom of the ring is nitrogen and the other is carbon, oxygen or nitrogen; or NR$^5$COR$^6$ together form a 4- or 5-membered lactam ring;

L is phenyl, phenyl-(C$_1$–C$_6$) alkyl, cinnamyl or pyridylmethyl, wherein the phenyl moieties of said phenyl and phenyl-(C$_1$–C$_6$) alkyl may be substituted with 1 to 3 substituents independently selected from the group consisting of (C$_1$–C$_6$) alkyl, (C$_1$–C$_6$) alkoxy, (C$_1$–C$_4$) alkoxycarbonyl, (C$_1$–C$_6$) alkylcarbonyl, —OCONR$^5$R$^6$, —NHCOOR$^5$, and halo; or L is a group of Formula 3:

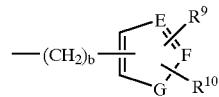

FORMULA 3 wherein b is an integer from 1 to 4; R$^9$ and R$^{10}$ are independently selected from the group consisting of hydrogen, (C$_1$–C$_4$) alkyl, halo, and phenyl; E and F are independently —CH— or nitrogen; and G is oxygen, sulfur or NR$^4$, with the proviso that when E and F are both nitrogen, one of R$^9$ and R$^{10}$ is absent; and R$^7$ and R$^8$ are independently selected from the group consisting of hydrogen, (C$_1$–C$_6$) alkyl, (C$_1$–C$_6$) alkoxycarbonyl, (C$_1$–C$_6$) alkylcarbonyl, and (C$_1$–C$_6$) alkoxy, with the proviso that said (C$_1$–C$_6$) alkoxy is not attached to a carbon that is adjacent to a nitrogen;

or a pharmaceutically acceptable salt or solvate thereof, and a pharmaceutically acceptable carrier.

16. The method of claim 1 or 10–15 wherein the companion animal is a cat or a dog.

* * * * *